United States Patent [19]

Everhart

[11] Patent Number: 5,275,280
[45] Date of Patent: Jan. 4, 1994

[54] DEVICE AND METHOD OF REMOVAL AND STORAGE OF SYRINGE NEEDLE

[76] Inventor: Shawn L. Everhart, 207 Willowbluff Dr., San Antonio, Tex. 78216

[21] Appl. No.: 880,242
[22] Filed: May 8, 1992
[51] Int. Cl.⁵ .............................................. B65D 83/10
[52] U.S. Cl. .................................. 206/366; 206/370; 206/365
[58] Field of Search ............ 206/63.5, 366, 365, 206/370; 604/110, 192; 220/908; 29/235

[56] References Cited

U.S. PATENT DOCUMENTS

| | | | |
|---|---|---|---|
| 4,667,821 | 5/1987 | Shillington | 206/366 |
| 4,738,362 | 4/1988 | Burns | 206/366 |
| 4,801,013 | 1/1989 | Bruno | 206/366 |
| 4,867,309 | 9/1989 | Germain | 206/366 |
| 4,869,366 | 9/1989 | Bruno | 206/370 |
| 4,922,597 | 5/1990 | Ikeda | 29/240 |
| 4,956,907 | 9/1990 | Bruno | 29/426.5 |
| 4,995,871 | 2/1991 | Sasaki et al. | 604/192 |
| 5,127,522 | 7/1992 | Ranford | 206/366 |

Primary Examiner—David T. Fidei
Attorney, Agent, or Firm—Gunn, Lee & Miller

[57] ABSTRACT

A method and device (10) is provided for safely removing a needle from the barrel of a syringe and for protectively storing the needle. A housing (16) contains V-shaped jaws (26) which are resiliently hinged, lined with a face of rubber or other gripping material, and biased towards a closed position. The round hub of the needle of a syringe is urged into the mouth (27) of the "V" until it is tight enough for the user to rotate the barrel without the hub and needle moving, thus disconnecting the needle from the syringe. A lever (44) engaging the housing (16) forces the jaws (26) to open, thus dropping the needle from the lid-mounted device into a container beneath.

4 Claims, 6 Drawing Sheets

DEVICE AND METHOD OF REMOVAL AND STORAGE OF SYRINGE NEEDLE

BACKGROUND

The present invention relates generally to devices for safely removing the needle portions of hypodermic needle/syringe assemblies and, more particularly, to a device which enables the safe removal of needles from a syringe assembly and also automatically provides safe storage of the needles for alternate disposal, substantially without risk of puncture or contact with the needles during removal, storage, or disposal. The present invention also relates to a one-hand method for safely disposing of needles using the device of the present invention thus decreasing the likelihood of inadvertent needle sticks.

More particularly, this invention concerns a disposable device for safely separating needles from barrels of syringes after use and for causing the separated needles to directly enter an impervious storage container, and a one-handed method for performing the operation safely.

BACKGROUND AND OBJECTS OF THE INVENTION

In hospital and other medical facilities, there is considerable use of hypodermic needles for administering medications and removing blood samples. Syringes are generally comprised of a cylindrical barrel having a nipple fitting at its lowermost extremity, a plunger slidably seated within the barrel, and the needle having a pointed distal extremity and a hub or base equipped with joining means for frictionally engaging the nipple. The needle is disengaged from the nipple of the barrel of the syringe by providing sufficient torque to overcome the friction of disengagement means between nipple and the hub of the needle.

In hospitals, waste may be segregated into two categories: medical waste and noninfectious/nonmedical waste. The significance of the difference between the categories is a series of state and federal regulations that more stringently regulate the disposal of medical waste as opposed to noninfectious/nonmedical waste. Therefore, it is advantageous for the hospitals to segregate medical waste from noninfectious/nonmedical waste and to minimize the medical waste. When a needle is used to inject a patient, because of its contact with the skin and blood of the patient, it becomes medical waste. However, the barrel of a syringe or the tube of an intravenous (IV) device, although attached to the needle during use, will be noninfectious/nonmedical waste, if not contaminated by blood. Thus the safe removal of the needle from the syringe or other device so as to properly store it and dispose of the device according to state and federal guidelines becomes important.

The tragic outbreak of the highly contagious AIDS disease, hepatitis, and other dangerous fluid or blood-borne diseases has highlighted the need for safer handling, storage, and disposal of such implements. In the case of disposable hypodermic needles, it had once been common practice to break or cut needle portions after use before discarding the needle and syringe. The purpose of this procedure was to reduce the overall size of the syringe assembly, eliminate the sharp point of the needle, and reduce the risk of puncture, scratch, or other injury which might otherwise result from handling. In breaking or cutting the needles, however, a substantial danger existed that an accidental puncture might occur during the breaking or cutting operation and this practice is now prohibited.

Nor does the process of recapping a needle reduce exposure of an accidental needle stick. The recapping of the contaminated needle is necessarily a two-handed operation. One hand holds the barrel of the syringe and the second hand moves the cap of the needle towards the needle. The recapping procedure, because of the proximity of the second hand holding the cap with the sharp, blood-contaminated needle, dramatically increases the likelihood of inadvertent needle sticks. Because of the danger of resheating or recapping a needle, the practice has been contraindicated for the Center of Disease Control and under OSHA guidelines. However, it is still advantageous to remove a contaminated needle from a noninfectious waste portion of the device so as to reduce the bulk and expense of properly disposing of the infectious wastes. What is needed is a safe device to remove the needle through the use of a one-hand method.

As a result of the foregoing dangers, it is current practice to dispose of such devices intact, without dismantling or capping them.

Thus, devices have been proposed and disclosed which are designed to safely remove and store needles from syringes. Such devices are generally comprised of means for dislodging the needle from the barrel of the syringe, and a container into which the dislodged needle falls by gravity. Thus, needle dislodging means have been disclosed which are associated with the upper lid of a needle storage container. These devices frequently utilize a moving jaw or jaws or equivalent means to grip the hub of the needle. The user generally employs the fingers of one hand to directly apply a pushing and squeezing force directly or indirectly upon the gripping means of jaws to secure the joining of the jaws to the needle, while the other hand is used to rotate the barrel and dislodge the hub from the nipple. Another approach for overcoming the foregoing difficulties involves the removal of the needle from its syringe so that the syringe (noninfectious/nonmedical waste) can be discarded with ordinary trash or refuse, while the needle (medical waste) is placed in a disposable storage receptacle placed at or near the patient's bed until it is full and can be properly disposed of. One device for practicing this method is sold under the name "SHARPS-Tainer" by Winfield Corporation of San Diego, Calif. This device includes a jar-like container with a snap-on lid to which is mounted a pliers-like, moving jaw device for grasping a needle hub and unscrewing it from the syringe. When the pliers-like device is opened the needle falls into the jar. Such a device necessarily requires the use of two hands. It is also relatively complicated and expensive to fabricate.

Another similar device is the "SHARPS Collector" sold by Becton Dickinson & Co. of Rutherford, N.J. This device includes a jar-like container with a snap-on lid. The lid includes a separate disc-like member rotatably sealed in the lid to allow circular movement when a needle is inserted into a slot formed in the disc and turned. The SHARPS Collector device includes a separate cover member for closing. This device, too, requires the operation of two hands, thus increasing the risk of an inadvertent needle stick by the user.

None of the devices disclosed, however, provide for a simple device without moving jaws, which can be easily fitted to a number of container lids without mutilation of the lid beyond providing a hole.

Moreover, none of the devices disclosed provide for a simple device without movable jaws, which device may be effectively and easily operated to remove the needle from the barrel of the syringe with only one hand, the hand holding the syringe.

Thus, it is the object of the present invention to provide for a simple device and a method which allows the user to insert the needle of a syringe into the mouth of a V-shaped pair of resilient jaw faces, to firmly place the hub of the needle into the mouth of the "V" until the sides of the hub grippingly contact the resilient jaws and to rotate the syringe until the barrel separates from the needle, then release the jaws from the hub.

This and other objects of the device and method of the present invention will be set forth below with reference to the specifications, drawings, and claims contained herein.

DETAILED DESCRIPTION OF THE PREFERRED EMBODIMENT

Figure 1:
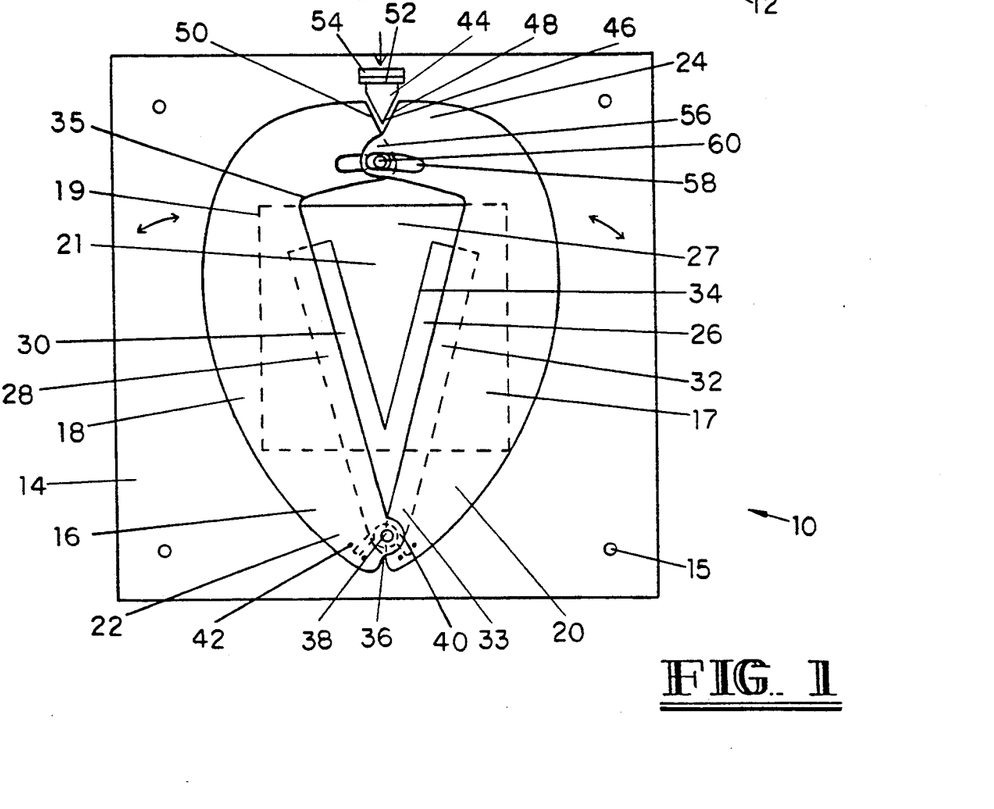
FIG. 1 is a top elevational view of a preferred embodiment of Applicant's present invention.

FIG. 1 illustrates in top elevational view a preferred embodiment of Applicant's needle-releasing device (10). More particularly, it can be seen that needle-releasing device (10) is affixed to a lid (12) (see FIG. 2) which is attached to a suitable needle-disposing container (not illustrated). Needle-releasing device (10) is preferably constructed of a generally tabular, square base (14) which is affixed by fasteners (15) such as rivets, screws or molded plastic pins or the like, to lid (12). Base (14) has housing means (16) thereon, housing means (16) overlying centrally-located base plate opening (17), base plate opening (17) being defined by inner walls (19) of base (14). Thus housing means (16) is composed of two shells, a left shell (18) and a right shell (20). Shells (18) and (20) have an overall shape when engaged as illustrated in FIG. 1, to that of a symmetrically-shaped apple. However, central to housing means (16) and defined by the inner walls (35) of shells (18) and (20) is needle insert opening (21). Each of shells (18) and (20) is similarly dimensioned and they engage one another at hinge end (22) and levered end (24). Contained partially within inner walls (35) of shells (18) and (20) are jaws (26). Jaws (26) are comprised of left leg (28) having left face (30) and right leg (32) having right face (34). Legs (28) and (32) meet at apex (33), thus defining a "V" shape. Jaws (26) may be made from rubber or other material suitable to grip the hub of the needle and may be serrated (see FIG. 7).

Apex (33) joins with hinge end (22) of shells (18) and (20) at hinge point (36). Hinge point (36) has hinge pin (38) affixed to base (14) and running vertically perpendicular thereto through both shells (18) and (20), as well as through apex (33) of jaws (26). Coiled around hinge pin (38) is bias means (40) such as a clip spring, as illustrated in FIG. 1, with two legs extending outward therefrom to be gripped by spring post holders (42) integral with and between the top and bottom surfaces of shells (18) and (20).

Thus it is seen that shells (18) and (20) comprising housing means (16) with jaws (26) therein are hingedly attached at hinge point (36) and maintained in a static position by bias means (40).

Turning now to levered end (24), it is seen how each of shells (18) and (20) are dimensioned to receive a release lever (44) dimensioned for receipt within a lever engagement bay (46). That is, release lever (44) formed integral with or attached hingedly to base (14) is designed for receipt within lever engagement bay (46) by engagement of release lever with right shell lever engagement wall (48) and left shell lever engagement wall (50). It can be seen that engagement walls (48) and (50) comprise a V-shaped opening defining lever engagement bay (46). It can also be seen in FIG. 1 how release lever (44) is dimensioned to be located substantially within lever engagement bay (46).

Release lever (44) is attached to base (14) by pivot means (52). Bias means (54) integral with base (14) urge release lever (44) toward and against lever engagement walls (48) and (50). Thus a dynamic balance is struck between the forces expanding the shells outward when release lever (44) is engaged with walls (48) and (50) and those of bias means (40).

As it can be appreciated, needle-releasing device (10) of the present invention is comprised of housing means (16) which contains jaws (26) between the top and bottom surfaces thereof. More specifically, jaws (26) are partially enclosed within the space between top and bottom surfaces of shells (18) and (20) and are attached thereto by glue, fasteners, or other conventional means. Jaws (26) are constructed in a V-shape, with mouth (27) broader than the hub of the needle of the syringe. Mouth (27) and inner walls (35) defining needle insert opening (21) are in communication with the interior of the container having lid (12) on the top surface thereof.

Jaws (26) are V-shaped and comprised of a flexible material which can flex outward to widen mouth (27). Jaws (26) have resilient faces (30), (34), that are either serrated or constructed of material that can grip the hub of the needle of the syringe. As legs (28) and (32) of jaws (26) flex, hinge point (36) allows shells (18) and (20) to pivot outward also. Thus, a nurse inserts a needle into needle insert opening (21) at mouth (27). Once the needle is inserted sufficiently so that the hub of the needle is adjacent faces (30) and (34), the nurse will then force the needle toward apex (33) until the hub of the needle firmly urges against faces (30) and (34). At this point there will be some give to the resilient faces as well as some flexing of the legs. This will cause some movement in the direction of the arrows indicated outward at hinge point (36). The natural resilience of jaws (26) as well as the effect of bias means (40) will be to resist, by compressional forces on the hub, the movement of the needle towards the apex. Once the hub is secure within and gripped by the faces, the nurse need only twist the barrel of the syringe to disengage the nipple of the syringe from the hub of the needle. The hub will remain firmly in place through the compressional forces acting on the hub where it contacts faces (30) and (34). The second step after removal of the needle from the springe is to disengage the needle from jaws (26). This is accomplished by compressing release lever (44) in the direction of the arrow indicated in FIG. 1. Forcing release lever (44) against lever engagement walls (48) and (50) forces shells (18) and (20) slightly outward, thus releasing the compression grip jaws (26) exert on the hub of the needle. This allows the needle to drop through needle insert opening (21) and through base plate opening (17) into the container below.

FIG. 1 also illustrates overlap portion (56). An overlap portion (56) provides for a portion of levered end (24) of left shell (18) and right shell (20) to overlap. Overlap portion (56) includes a guide slot (58) with a guide pin (60) inserted therein. The combination of overlap portion (56) with guide slot (58) and guide pin (60) provides a means to keep shells (18) and (20) properly and laterally aligned during use of needle releasing instrument (10). Note that in this particular embodiment, left shell (18) provides for the mounting of guide pin (60) where right shell (20) has guide slot (58) therein.

Figure 2:
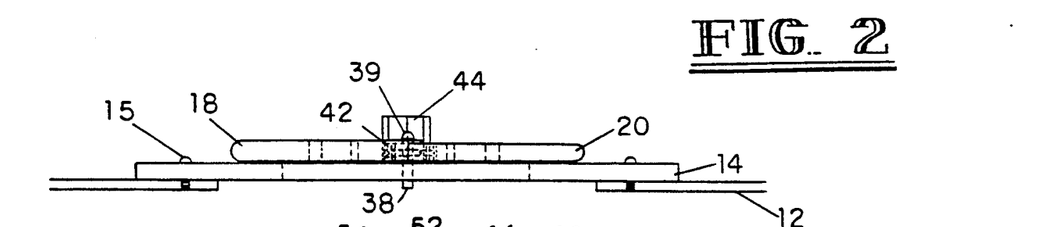
FIG. 2 is a cut-away side elevational view of a preferred embodiment of Applicant's present invention.

FIG. 2 provides a cut-away elevational view to Section A-A' of the embodiment illustrated in FIG. 1. FIG. 2 shows how left shell (18) overlaps right shell (20) at hinge pin (38) to provide a unitary housing means (16). Also illustrated is the manner in which bias means (40) engages spring post holders (42) through use of hinge pin (38). Note also how hinge pin (38) has hinge pin holder (39), such as a clip, to hold shells (18) and (20) in place on base (14). The combination of hinge pin (38) anchoring housing means (16) to base (14) and the action of bias means (54) urging release bar (44) into lever engagement bay (46), provides for the stability of housing means (16) on base (14) so that it does not rotate about hinge point (36) during use.

Figure 3:
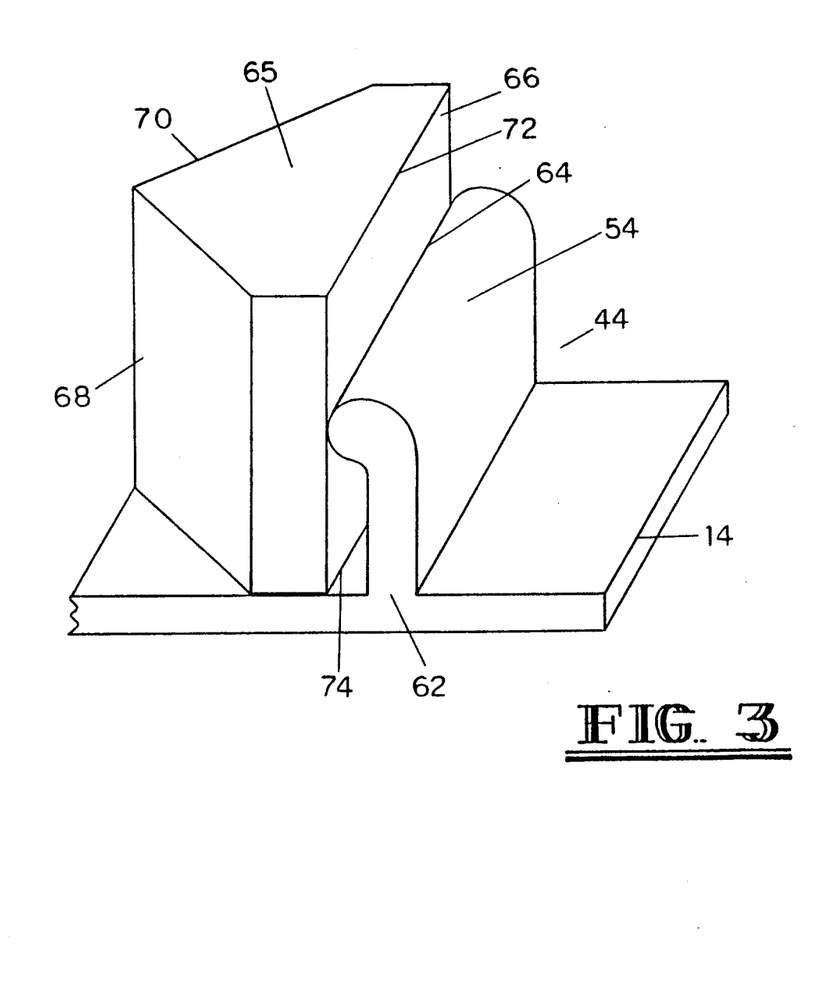
FIG. 3 is a perspective side view of the release lever of Applicant's present invention as removed from the device itself.

FIG. 3 provides additional details of the manner in which release lever (44) is designed. Bias means (54) is seen to be molded integral with base (14). Moreover, bias means (54) is seen to have a generally tabular body portion (62) with a curved lip (64) on the top surface thereof. Release lever (44) has a rear wall (66) engageable with curved lip (64). Release lever (44) is also comprised of a body (65) having release lever faces (68) and (70) coming to a point as illustrated in FIG. 3. In particular, note that body (65) is wedge shaped, providing for release faces (68) and (70) dimensioned to fit within lever engagement bay (46) (FIG. 1). Release lever (44) has a top edge (72) of rear wall (66) that preferably stands above housing means (16) (see FIG. 1). Release lever (44) is attached hingedly to base (14) along lower edge (74). Preferably, release lever (44) and bias means (54) are formed of plastic integral with base (14).

In use, curved lip (64) engages rear wall (66) along a lower portion thereof to urge body (65) into lever engagement bay (46) such that release faces (68) and (70) engage walls (48) and (50) of lever engagement bay (46). In a nonuse position there will be an equilibrium in the system between release lever (44) as it tends to hold the top portion of housing means (16) in place with bias means (40) and the natural resiliency of jaws (26). However, forcing the hub of a needle into the "V" so as to engage the jaws will tend to rotate lever end of housing means shells (18) and (20) apart. After disengagement of the needle from the hub, pressing top edge (72) of release lever (44) into lever engagement bay (46) and against walls (48) and (50) will provide further widening of jaws (26), allowing needle to drop into the container below.

Figure 4:
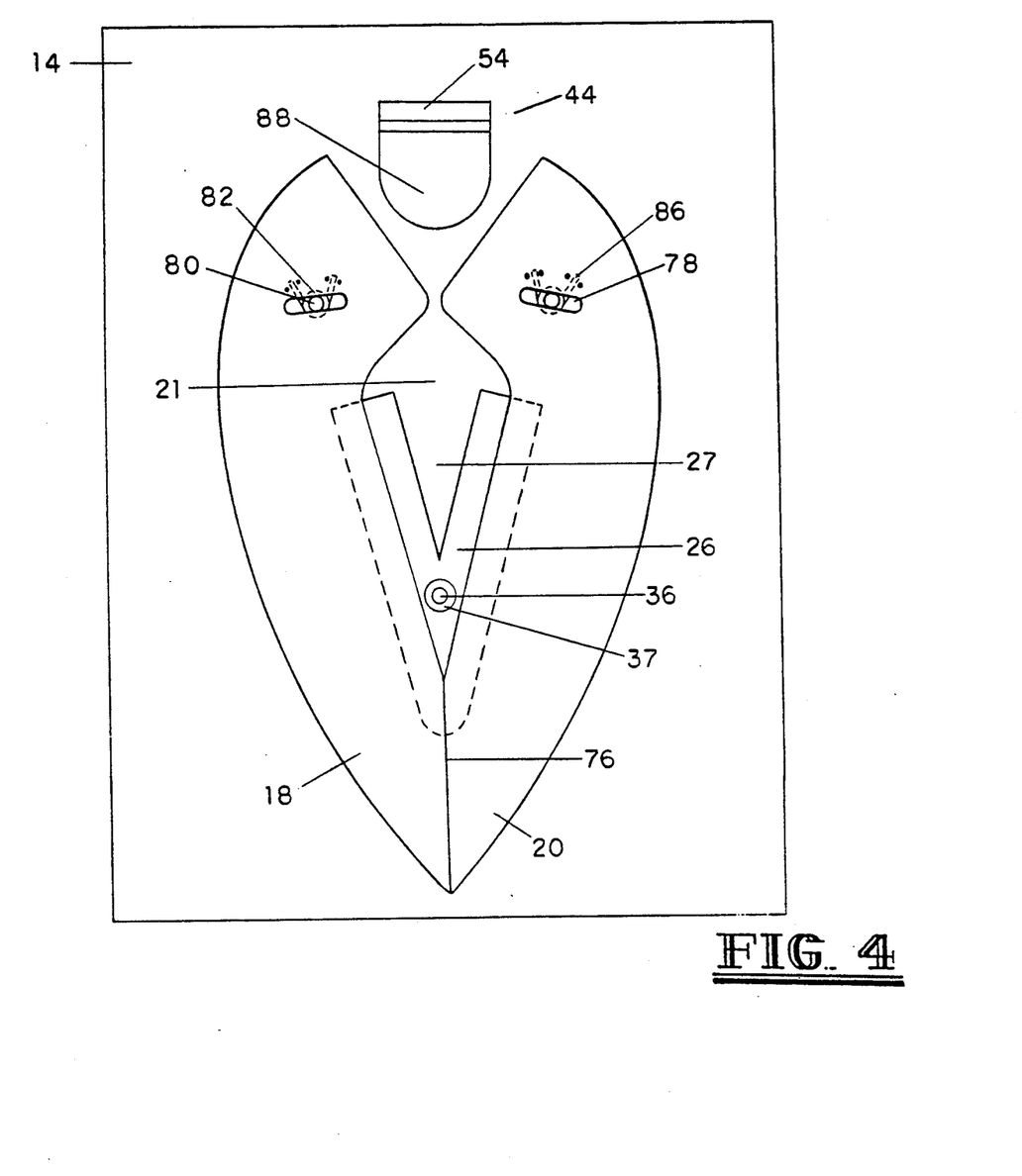
FIGS. 4, 5, 6 and 7 are all top elevational views of alternate preferred embodiments of Applicant's present invention.
Figure 5:
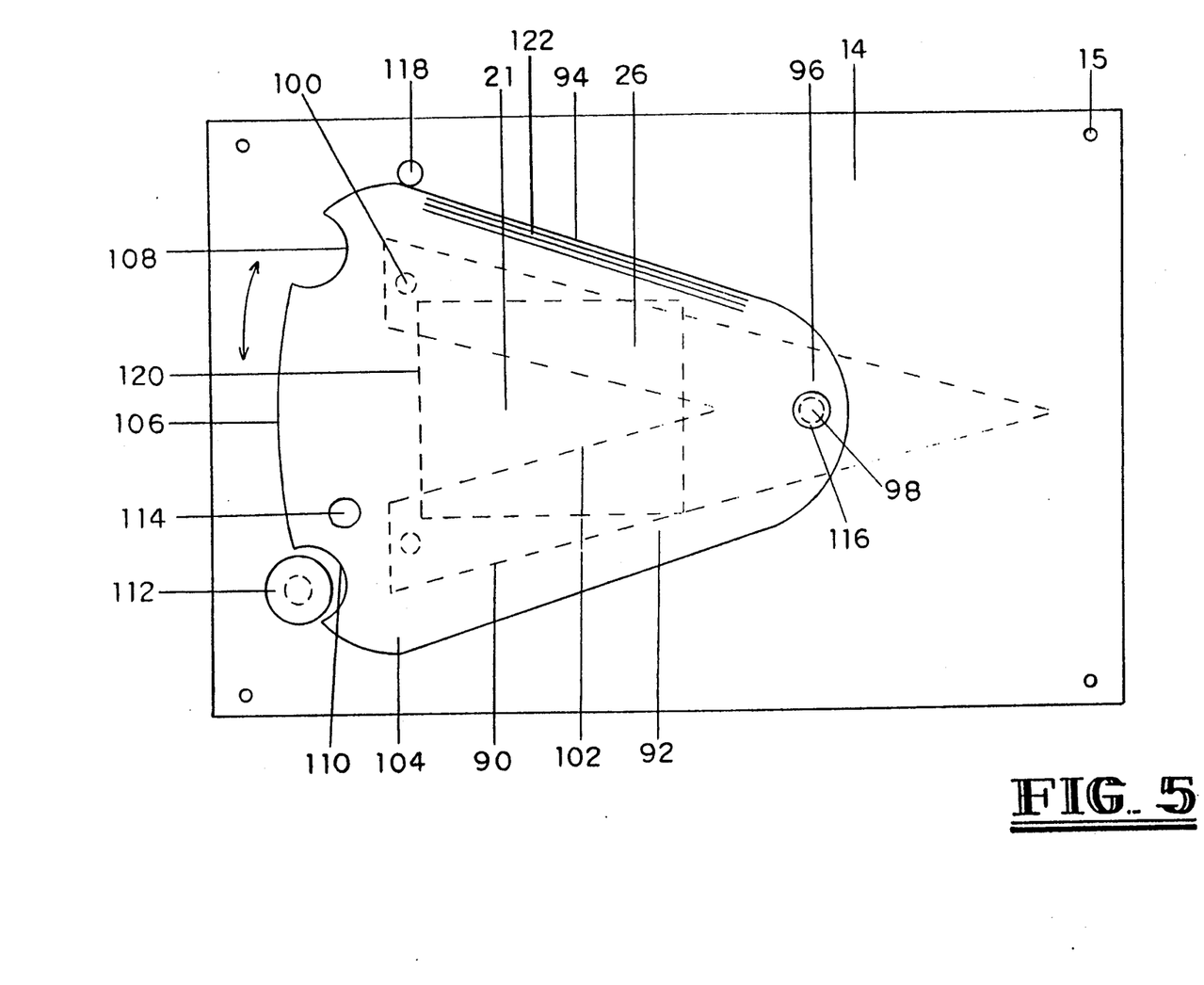
Figure 6:
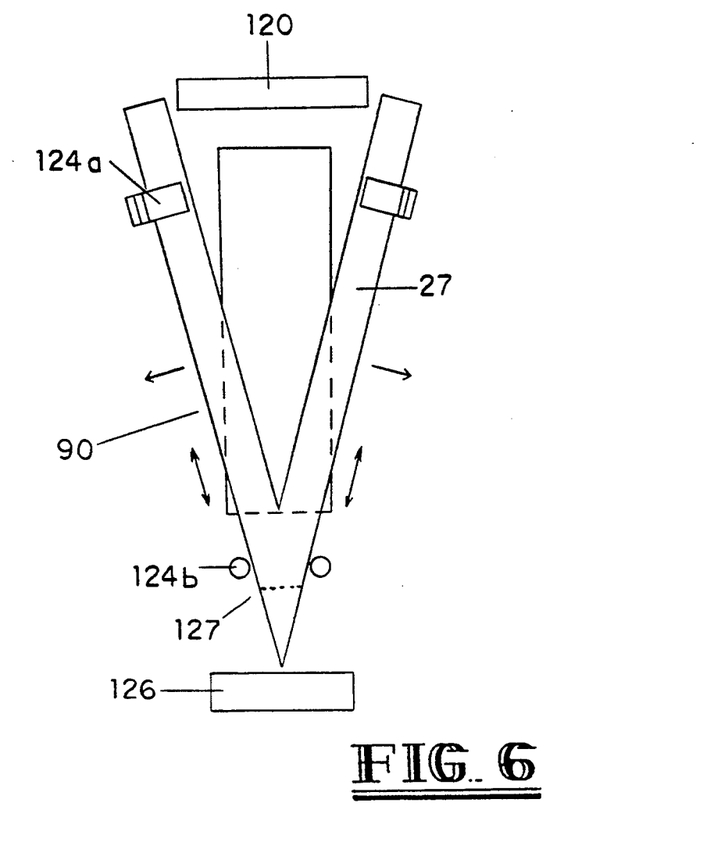

FIGS. 4, 5, and 6 provide additional preferred embodiments of Applicant's invention. However, all embodiments illustrated in the specifications provide for the novel V-shaped resilient jaws. They may be configured with or without housing, with or without bias springs, etc. Indeed, in a simple embodiment, illustrated in FIG. 6, there are no pivoting shells or housing, or levers provided.

Turning now, however, to FIG. 4, it is seen that housing means (16) may be provided with left shell (18) and right shell (20) which, instead of being provided with the hinge point and hinge pin are simply attached with a resilient hinge member (76), thus housing means (16) as illustrated in FIG. 4 may be manufactured unitarily or in one piece. Jaws (26) are provided as in FIG. 1, with the entire unit affixed to a base through hinge pin (36) and held by hinge pin clip (37). Note however, in the embodiment illustrated in FIG. 4, the use of guide channels (78) in both upper and lower surfaces of left shell (18) and right shell (20). Extending through both guide channels of both shell halves are guide posts (80) with guide post clip (82) attached to the top thereof. This system of channels, posts and clips provides two functions. First, it allows for left shell (18) and right shell (20), as they open and close in use, to be guided and aligned with the base. Second, it provides for a stability, along with release lever (44) and hinge pin (36) to hold or position housing means (16) to base (14) so it does not flop around while in use. Note also that optional clip springs (not shown) may be provided between the top and bottom surface of both left shell (18) and right shell (20) to positionally maintain with a positive bias means the width of V-shaped jaws (26).

Of course, a similar system could be used instead of or in addition to overlap portion (56) as illustrated in FIG. 1 on any of the embodiments illustrated. Additionally, note the use of release lever (44) having semicircular release liner face (88) in lieu of wedge-shaped release lever faces (68) and (70). This is an alternate preferred embodiment of release lever (44) which could be used as well in the embodiment illustrated in FIG. 1. The principal, function and use of release lever (44) and needle release in device (10) as illustrated in FIG. 4 is the same as that embodiment illustrated in FIG. 1.

An even simpler means of using Applicant's novel, V-shaped resilient jaws is illustrated in FIG. 5 which provides for simply a jaw holder (90) which is comprised of a strip of plastic or other resilient material bent into a V-shape defined by left wall (92), right wall (94) and apex (96). On the inner faces of left wall (92) and right wall (94) are located jaws (26) which may be made of a resilient and/or gripping material so as to engage the hub of the needle when it is firmly urged from mouth (27) in towards apex (96). Pivot pin (98) and fasteners (100) simply hold the entire jaw/jaw holder assembly fixedly to base (14). In use, forcing the hub of the needle into the mouth toward apex (96) until it engages hub engagement ridges (102) of jaws (26) will provide for flexure of left wall (92) and right wall (94) outward. After twisting off the needle from barrel, the needle will be released by asserting a force at apex (96) which will cause further bowing (slightly) of walls (92) and (94) outward, allowing jaws (26) to release needle to fall through base (14) into container below.

FIG. 5 provides an additional feature which may be found on any of the other embodiments illustrated herein as well. That is, a cover (104) which is pivotally located to pivot point (98) and is generally V-shaped and held snugly flat against jaws (26) so as to provide a cover preventing access to needle insert opening (21) when cover is in the closed position (as illustrated). Cover (104) has a removed edge (106), which has notch for open (108) and a notch for close (110) which is engaged through notch engagement post (112). Handle (114) near removed edge (106) provides a means for sliding cover (104) between a closed and an open position (see arrows), the open position allowing access to jaws (26). Cover (104) may also have a holding clip (116) to maintain cover (104) in the closed position against a stop post (118). Wall (120) provides substantially complete closure to needle insert opening (21) as it extends across, between the inner faces of jaws (26). On the inside surface of cover (104) is located hub engagement ridge (122). Thus, when the hub has been released and is held in jaws (26), closure of cover (104) will allow hub engagement ridge (122) to engage the top portion of the hub that lies above jaws (26). As can be seen in FIG. 5, the angle at which ridge (122) engages the hub will provide a force to the hub, moving it toward the open mouth (27) of jaws (26) and thus allow it to be released and dropped to the container below. Preferably, cover (104) is made of clear plastic to allow the nurse to view whether the disengagement of the needle by the jaws (26) has been effected.

Figure 6A:
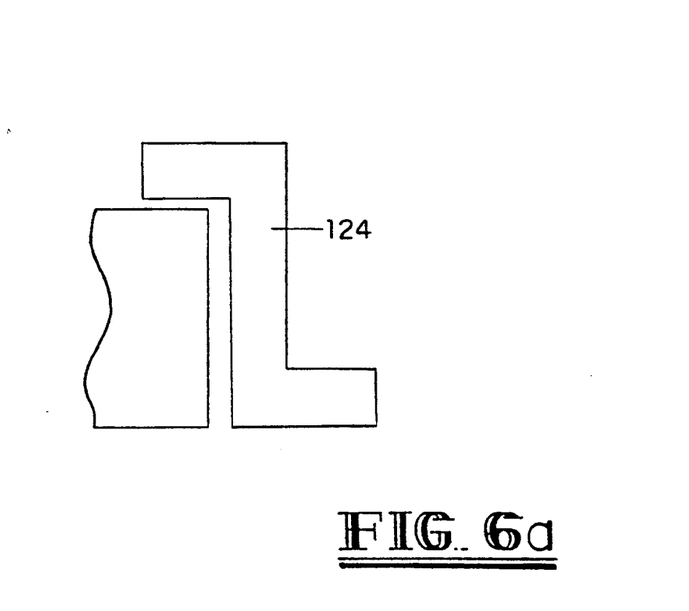
FIG. 6a is a side elevational view of hold-downs (124).

Turning now to FIG. 6, an illustration of perhaps an even simpler version of Applicant's device, it can be seen that jaw holder (90) with jaws on the inner faces thereof may be simply held in place on base (14) by hold-downs (124a) (see FIG. 6a). This embodiment will allow jaw holder (90) to actually slide slightly downward toward apex stop (126) (see arrows) while the hub is being firmly urged into the jaws. Upon striking apex stop (126), jaws will be forced open and the compressive force will allow the nurse to disconnect the needle. Release is effected simply by pressing apex stop (126) and allowing slight movement of jaw holder (90) upward toward wall (120). Wall (120) engages the inner face of jaws (27) inside of leg hold-downs (124a). Such a movement upward, as illustrated in FIG. 6, will tend to first release then force jaws (27) slightly apart and allow for release of needle into container below. This embodiment could be simplified even further by truncating the pointed end of jaw holder (90) as indicated with dashed lines (127) and eliminating apex stop (126). The user will simply place a finger at the truncated portion and urge the jaws upward (as seen in FIG. 6) to release the needle.

Figure 7:
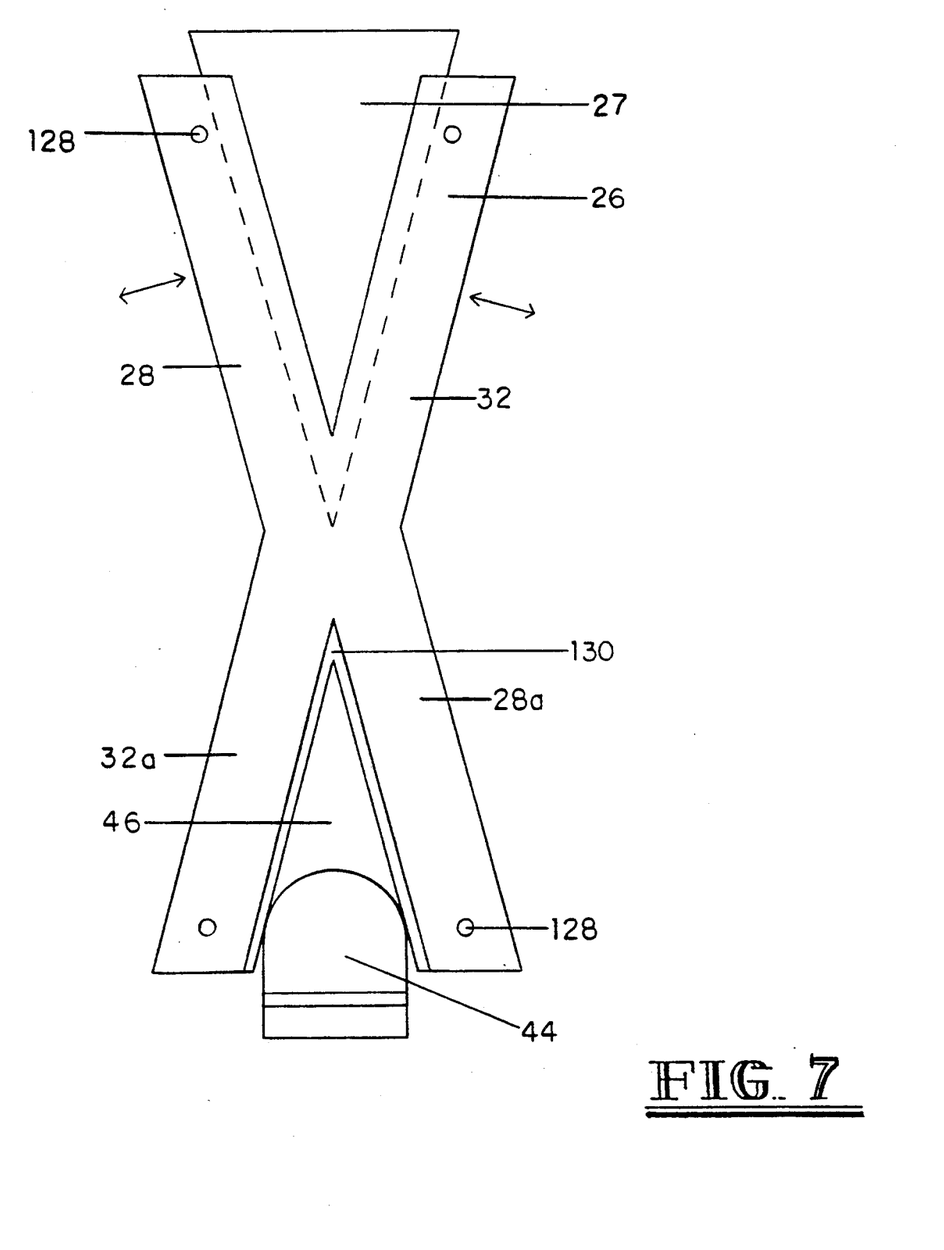

Turning now to FIG. 7, Applicant provides for V-shaped jaws (26) held to lid (12) by pins (128). Note in the embodiment illustrated in FIG. 7 that while the jaws are generally V-shaped, legs (28) and (32) extend distally to removed portions (28a) and (32a) which provide for lever engagement bay (46) having force transmittal member (130) to carry force provided by release lever (44) to V-shaped jaws (26), thereby providing an outward flexing of legs (28) and (32) so as to release the needle grasped therebetween.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

I claim:

1. A device for the removal of needles from syringes, the device comprising:
   a closed container with a lid, the lid of said closed container having an opening therein;
   housing means, mountable to the lid of said container, said housing means having two members resiliently joined at a hinge portion and having walls defining a central open portion wherein said members further comprises adjacent walls defining a lever engagement bay dimensioned and located for a lever to engage the housing means;
   jaw means for gripping the hub of a needle syringe, said jaw means having a pair of faces defining a "V" shape, the open end of said "V" of said pair of faces being wider than the hub of the needle, said jaw means dimensioned for receipt within said housing means such that said pair of faces lie substantially within the open portion of said housing means;
   wherein the open portion of said housing means overlies the opening of said lid such that when the hub is firmly urged into the open end of the V-shaped pair of faces toward the apex of the "V", the hub of the syringe contacts the faces and the barrel may be rotated without twisting the hub, thereby securing the release of said needle;
   a base on which to mount said jaw means and housing means, said base for mounting to said lid; and
   release means for urging said jaw means outward allowing for release of the needle, wherein said release means comprises a lever hingedly attached to said base.

2. The device of claim 1 wherein walls of the lever engage the adjacent walls of the members defining the lever engagement bay so as to force said housing means members outward.

3. The device of claim 2 further comprising bias means engaging said housing means so as to resist the movement of the members of said housing means outward.

4. The device of claim 3 further comprising means to urge the lever of said release means against the adjacent walls defining the lever engagement bay of said members.

* * * * *